US010238512B2

(12) United States Patent
Frid

(10) Patent No.: US 10,238,512 B2
(45) Date of Patent: Mar. 26, 2019

(54) MRI VISIBLE MEDICAL DEVICE

(71) Applicant: CARDIATIS S.A., Isnes (BE)

(72) Inventor: Haroun Frid, Brussels (BE)

( * ) Notice: Subject to any disclaimer, the term of this patent is extended or adjusted under 35 U.S.C. 154(b) by 400 days.

(21) Appl. No.: 14/769,767

(22) PCT Filed: Feb. 21, 2014

(86) PCT No.: PCT/EP2014/053476
§ 371 (c)(1),
(2) Date: Aug. 21, 2015

(87) PCT Pub. No.: WO2014/128276
PCT Pub. Date: Aug. 28, 2014

(65) Prior Publication Data
US 2016/0022443 A1 Jan. 28, 2016

(30) Foreign Application Priority Data
Feb. 22, 2013 (EP) .................... 13156291

(51) Int. Cl.
*A61F 2/82* (2013.01)
*A61L 31/08* (2006.01)
(Continued)

(52) U.S. Cl.
CPC ............... *A61F 2/82* (2013.01); *A61F 2/01* (2013.01); *A61F 2/2418* (2013.01);
(Continued)

(58) Field of Classification Search
CPC ........ A61F 2210/009; A61F 2250/0096; A61F 2/01; A61F 2/2418; A61F 2/82;
(Continued)

(56) References Cited

U.S. PATENT DOCUMENTS 5,326,637 A * 7/1994 Nasu ................... G11B 5/656
204/192.2
7,588,597 B2 9/2009 Frid
(Continued)

FOREIGN PATENT DOCUMENTS

| WO | WO-2006003639 A1 * | 1/2006 | ............ B82Y 25/00 |
| WO | WO 2006/094941 A1 | 9/2006 | |
| WO | WO 2012/033637 A1 | 3/2012 | |

OTHER PUBLICATIONS

Cabo, M. et al. "Synthesis of Compositionally Graded Nanocast NiO/NiCo2O4/Co3O4 mesopourous composites with tunable magnetic properties"; Journal of Materials Chemistry, vol. 20, 2010, pp. 7021-7028.
(Continued)

Primary Examiner — Jenny R Wu
(74) Attorney, Agent, or Firm — Leydig, Voit & Mayer, Ltd.; Gerald T. Gray

(57) ABSTRACT

Cobalt in oxidized state for use as anti-artifact layer (4) covering a metallic substrate (1) of a medical device for reducing the production of artifacts in MRI caused by the magnetic property of the (1), wherein the anti-artifact layer (4) is present at outermost surface of the metallic substrate (1) and has at least 30% of cobalt ratio (at % Co) to the total amount of transition metallic atoms present therein, and at least 90% of cobalt atoms present within the anti-artifact layer (4) are converted into at least one of Co(II) oxidized state and Co(III) oxidized state.

18 Claims, 3 Drawing Sheets

(51) Int. Cl.
| | |
|---|---|
| *C23C 14/34* | (2006.01) |
| *A61F 2/01* | (2006.01) |
| *C23C 14/22* | (2006.01) |
| *A61L 31/02* | (2006.01) |
| *A61L 27/04* | (2006.01) |
| *A61L 27/30* | (2006.01) |
| *A61L 27/50* | (2006.01) |
| *A61L 29/02* | (2006.01) |
| *A61L 29/10* | (2006.01) |
| *A61L 29/14* | (2006.01) |
| *A61L 31/14* | (2006.01) |
| *A61F 2/24* | (2006.01) |

(52) U.S. Cl.
CPC ............. *A61L 27/045* (2013.01); *A61L 27/30* (2013.01); *A61L 27/50* (2013.01); *A61L 29/02* (2013.01); *A61L 29/10* (2013.01); *A61L 29/14* (2013.01); *A61L 31/022* (2013.01); *A61L 31/082* (2013.01); *A61L 31/088* (2013.01); *A61L 31/14* (2013.01); *C23C 14/221* (2013.01); *C23C 14/34* (2013.01); *A61F 2210/009* (2013.01); *A61F 2250/0096* (2013.01); *A61L 2420/02* (2013.01)

(58) Field of Classification Search
CPC .... A61L 2420/02; A61L 27/045; A61L 27/30; A61L 27/50; A61L 29/02; A61L 29/10; A61L 29/14; A61L 31/022; A61L 31/082; A61L 31/088; A61L 31/14; C23C 14/221; C23C 14/34

See application file for complete search history.

(56) References Cited

U.S. PATENT DOCUMENTS

| | | | |
|---|---|---|---|
| 2003/0026894 A1* | 2/2003 | Narisawa | B82Y 10/00 427/128 |
| 2009/0054981 A1* | 2/2009 | Frid | G01R 33/28 623/11.11 |

OTHER PUBLICATIONS

Getzlaff, M. et al., "Spin Resolved Photoemission Study of Oxygen on Thin Cobalt Films", Journal of Electron Spectroscopy and Related Phenomena, vol. 77, 1996, pp. 197-207.

Peng, D.L. et al., "Preparation and Magnetic Properties of Oxide-Coated Monodispersive Co Cluster Assemblies", Physica. Status Solidi. (A), vol. 172, 1999, pp. 209-216.

International Search Report, PCT/EP2014/053476, performed within the European Patent Office dated Mar. 7, 2014.

* cited by examiner

MRI VISIBLE MEDICAL DEVICE

CROSS-REFERENCE TO RELATED APPLICATIONS

This application is a U.S. national phase of International Patent Application No. PCT/EP2014/053476, filed Feb. 21, 2014, which claims the benefit of European Patent Application No. 13156291.0, filed Feb. 22, 2013, the disclosure of which is incorporated by reference in its entirety.

TECHNICAL FIELD

The present invention relates to medical devices comprising a metallic substrate that is magnetic resonance image compatible, more particularly, to medical devices comprising a metallic substrate which have an anti-artifact layer at the outermost surface of the metallic substrate wherein the anti-artifact layer reduces the production of artifacts in magnetic resonance imaging (MRI).

BACKGROUND OF THE INVENTION

The perfecting of imaging processes has caused important progresses in medicine. Nuclear magnetic resonance imaging (MRI) is desirable alternative to invasive angiography. It allows making visible tissues and blood vessels. For example, cardiac MRI has been shown to provide accurate image of the proximal and medial parts of the coronary arteries. Since the presence of contrast agents or anesthetics is not necessary for MRI-based angiography, there is minimal risk of complications with MRI. One of the advantages of MRI is that the blood flow can be assessed quantitatively. This flow information can provide important data concerning i.a. the presence of stenosis in the vessel. However, MRI does have some limitations in the presence of conventional metallic medical devices. For instance, medical devices such as vascular prosthesis and stents often comprise, or essentially consist of, a metallic substrate in order to obtain adequate mechanical properties, and the ferro- or ferrimagnetic (FFM) properties of the metallic substrate cause the production of artifacts. An artifact is a feature appearing in an image that is not present in the original object and it can misrepresent the anatomy under diagnosis using MRI by either partially or completely blocking out the desired image in the vicinity of the metal parts.

For example, after a stent has been introduced in a vessel of a patient, it is generally advisable to continuously monitor its efficiency in order to detect any undesirable in-stent restenosis. However, since stents often comprise metal parts (wire or plates), excessive signal loss is observed inside and close to the stent.

US 2005/0276718A discloses a biocompatible alloy used for implantable medical device, wherein the MRI compatibility of the alloy is improved by reducing the iron and/or silicon contents thereof. Namely, the MRI compatibility of an alloy has been improved by optimizing the composition ratio of the alloy per se.

EP 1864149 discloses a stent exhibiting reduced interference in MRI. The stent consists of NiTi alloy such as Nitinol containing at least 50 weight percent of nickel (wt % Ni). The exterior surface of stent is modified so as to be covered with an oxide layer wherein all nickel atoms present in the oxide layer are oxidized into nickel monoxide (NiO). This document also discloses a method for providing a nickel monoxide layer at the exterior surface of Nitinol. This method is only applicable to the nickel-based alloy comprising at least 50 wt % Ni.

Ferromagnetism is the basic mechanism by which certain materials form permanent magnets, or are attached to magnets. In physic, several different types of magnetism are distinguished. Ferromagnetism including ferrimagnetism is the strangest type; it is the only type that creates forces strong enough to be felt, and is responsible for the common phenomena of magnetism encountered everyday life. For example, cobalt, iron and nickel are known as ferromagnetic material in its metallic state. Some metals such as iron and chromium are known as ferri- or ferro-magnetic (FFM) material in its oxidized state.

A significant portion of stents used in a clinical setting are made of cobalt-based alloy, such as Phynox, Elgiloy and Cobalt-Chromium. Usually a cobalt-based alloy has high atom concentration of cobalt and often chromium which are ferromagnetic materials in its metallic state or its oxidized state, and produce strong artifacts in MRI. If an alloy does not have a sufficient concentration of nickel comparing to the FFM material(s) present in the alloy, the conventional method of providing nickel monoxide layer as an anti-artifact layer is not applicable. Furthermore, if an alloy comprises a metal which exhibits the FFM property in its oxidized state, e.g., chromium oxide and iron oxide, simply converting all metal present at the outermost surface of the alloy into oxidized state in order to obtain an oxide layer including NiO is not always sufficient to obtain a sealing (masking) effect of the FFM property of the alloy for MRI visibility because it may increases the surface concentration of FFM material in its oxidized state.

Therefore, a new composition used as anti-artifact layer deposited at the outermost surface of a metallic substrate, particularly an alloy comprising (a) less than 50 wt % Ni or without Ni and (b) metal(s) which exhibits the FFM property in its oxidized state, is desired. Furthermore, a method for providing an anti-artifact layer at the outermost surface of said metallic substrate is longed for. The object of the present invention is to provide a solution for satisfying the requirements mentioned above.

SUMMARY OF THE INVENTION

The object of the present invention is to provide medical devices comprising, or essentially consisting of, a metallic substrate with MRI compatible property.

Another object of the present invention is to use a cobalt-rich composition as anti-artifact layer continuously covering a metallic substrate which comprises at least one of chromium and iron for reducing the production of artifacts in magnetic resonance imaging (MRI) caused by ferro- or ferri-magnetic (FFM) property of the metallic substrate.

The subject-matter of the present invention is defined in the appended independent claims. Preferred embodiments are defined in the dependent claims.

A subject matter of the present invention is a medical device comprising a metallic substrate which comprises cobalt and at least one of metals which exhibit ferro- or ferri-magnetic (FFM) property in its oxidized state such as chromium and iron. The metallic substrate contains an oxide layer at the outermost surface of the metallic substrate. The oxide layer has at least 50% of cobalt-atomic percent (at % Co) to the total amount of metallic atoms which exhibit FFM property in its oxidized state, present within 10 nm from the external surface of the oxide layer. At least 90% of cobalt atoms present within 10 nm from the external surface of the oxide layer are oxidized into at least one of Co(II) and Co(III) oxidized state. At least 55% of cobalt atoms present within 10 nm from the external surface of the oxide layer are at least one of cobalt monoxide (CoO) or cobalt (II,III) oxide ($CoO.Co_2O_3$).

According to an advantageous embodiment, at least 95% of cobalt atoms, preferably all cobalt atoms, present within 10 nm from the external surface of the oxide layer are oxidized into at least one of Co(II) oxidized state and Co(III) oxidized state Advantageously said oxide layer has at least 60% of cobalt-atomic ratio (at % Co) to the total amount of metallic atoms which exhibit FFM property in its oxidized state, present within 10 nm from the external surface of the oxide layer, preferably 70 at % Co, more preferably 80 at % Co, even more preferably 100 at % Co, most preferably 120 at % Co so as to have improved anti-artifact property.

Preferably, the oxide layer further comprises at least 50 at % Co to the total amount of metallic atoms which exhibit FFM property in its oxidized state present between 10 and 1000 nm from the external surface of the oxide layer, and at least 90% of cobalt atoms present within at least 100 nm, preferably within at least 500 nm, more preferably within at least 1000 nm, from the external surface of the oxide layer can be oxidized into at least one of Co(II) oxidized state and Co(III) oxidized state.

The medical device according to the present invention is implantable and preferably selected from a group consisting of vascular endoprosthesis, intraluminal endoprosthesis, stents, coronary stents and peripheral stents.

The metal substrate is advantageously made of a biocompatible alloy selected from the group consisting of nickel titanium alloys such as nitinol, copper zinc aluminium alloys, stainless steels such as Cr—Ni—Fe steel, and Co—Cr alloys such as Phynox, Elgiloy and Cobalt-Chromium.

The outermost layer of the metallic substrate preferably has at least 50 at % Co to the total amount of metallic atoms which exhibit FFM property in its oxidized state present in the outermost layer. Furthermore, at least 90% of cobalt atoms present in the outermost layer is preferably oxidized into at least one of Co(II) and Co(III) oxidized state and at least 60% of cobalt atoms present therein are at least one of cobalt monoxide (CoO) or cobalt (II,III) oxide ($CoO.Co_2O_3$). A ratio of the thickness ($T_{(4)}$) of the outermost layer to the thickness ($T_{(1)}$) of metallic substrate is preferably at least 1/80000 ($T_{(4)}/T_{(1)}$), more preferably 1/8000, even more preferably 1/4000, most preferably 1/800.

Another subject of the present invention is a method for providing a metallic substrate with an anti-artifact property in MR imaging comprising following steps of (a) providing the metallic substrate, (b) forming a cobalt-rich layer at outermost surface of the metallic substrate, wherein the cobalt-rich layer comprises at least 50% of cobalt-atomic percent (at % Co) to the total amount of metallic atoms which exhibit FFM property in its oxidized state present therein, and (c) converting at least 90% of cobalt atoms present within at least 10 nm from the external surface of the metallic substrate into at least one of Co(II) oxidized state and Co(III) oxidized state, and at least 55% of cobalt atoms present therein into at least one of cobalt monoxide (CoO) or cobalt (II,III) oxide ($CoO.Co_2O_3$).

The cobalt-rich layer preferably comprises at least 60%, preferably 70%, more preferably 80%, even more preferably 100%, most preferably 120%, of cobalt-atomic ratio (at % Co) to the total amount of metallic atoms which exhibit FFM property in its oxidized state present therein.

In step (a), the metallic substrate is preferably in a form selected from a group consisting of wire, plate, cylinder and any shape of implantable medical devices such as stent and artificial joint.

If the metallic substrate is a cobalt-based alloy, it is advantageously subjected to a thermal treatment at a temperature at least 500° C., preferably at least 550° C., for at least at least 3 hours in step (b) so as to form a cobalt-rich layer on the metallic substrate.

In step (b), the metallic substrate is preferably subjected to physical vapor deposition (PVD) with a target which comprises cobalt, so as to form a cobalt-rich layer on the metallic substrate.

In steps (b), the metallic substrate is preferably subjected to physical vapor deposition (PVD) with a target comprising cobalt in presence of oxygen, so as to form a cobalt-rich and cobalt oxide(s) layer on the metallic substrate.

Advantageously, PVD is selected from a group consisting of sputter deposition, evaporative deposition, pulsed laser deposition, electron beam physical vapor deposition, and cathodic arc deposition.

The thickness of the cobalt-rich layer comprising at least 50% of cobalt-atomic percent (at % Co) to the total amount of metallic atoms which exhibit FFM property in its oxidized state present therein is advantageously at least 1 nm, preferably at least 5 nm, more preferably at least 10 nm, even more preferably at least 50 nm, still even more preferably at least 100 nm, most preferably at least 500 nm.

In step (c), the metallic substrate is preferably subjected to an ethylene oxide atmosphere in a concentration between 500 mg/L and 1 g/L saturated with water at between 40° C. and 60° C. for at least 5 hours, preferably at least 10 hours.

Another subject of the present invention relates to a use of cobalt oxides as anti-artifact layer covering a metallic substrate for reducing the production of artifacts in magnetic resonance imaging (MRI) caused by the FFM property of the metallic substrate, wherein the anti-artifact layer is present at outermost surface of the metallic substrate and has at least 50% of cobalt ratio (at % Co) to the total amount of metallic atoms which exhibit the FFM property in its oxidized state present therein, at least 90% of cobalt atoms present within the anti-artifact layer are converted into at least one of Co(II) oxidized state and Co(III) oxidized state, and at least 55% of cobalt atoms present therein into at least one of cobalt monoxide (CoO) or cobalt (II,III) oxide ($CoO.Co_2O_3$).

Still another aspect of the present invention relates to a use of cobalt in oxidized state as anti-artifact layer covering a metallic substrate of a medical device for reducing the production of artifacts in MRI caused by FFM property of the metallic substrate, such as chromium and iron, wherein the anti-artifact layer is present at outermost surface of the metallic substrate and has at least 50% of cobalt ratio (at % Co) to the total amount of metallic atoms present which exhibit the FFM property in its oxidized state, therein, at least 90% of cobalt atoms present within the anti-artifact layer are converted into at least one of Co(II) oxidized state and Co(III) oxidized state, and at least 55% of cobalt atoms present therein into at least one of cobalt monoxide (CoO) or cobalt (II,III) oxide ($CoO.Co_2O_3$).

DESCRIPTION OF THE INVENTION

Figure 1:
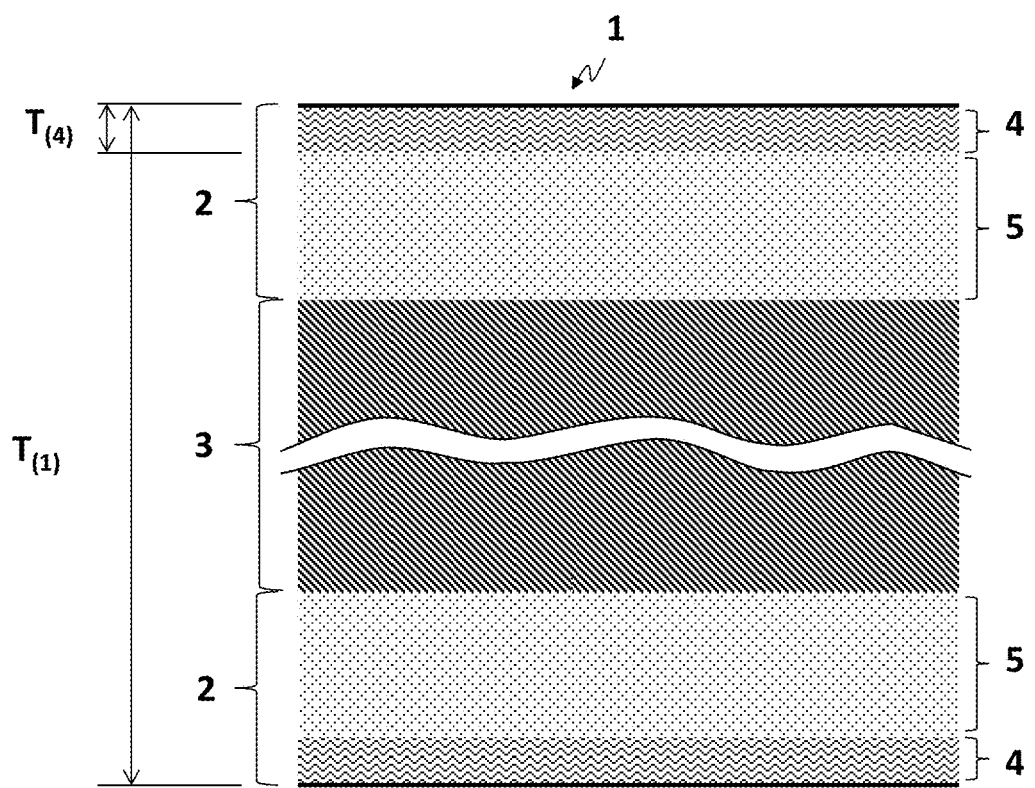
FIG. 1 shows a schematic diagram of a cross section of a portion of a metallic substrate having an anti-artifact layer(s) at the outermost surface of the metallic substrate according to the present invention.

The term of "magnetic resonance imaging (MRI)" means in the present invention the use of nuclear magnetic resonance to produce images of the molecules that make up a substance, for example the soft tissues of the human or animal body.

According to a preferable embodiment, a "medical device" is understood to include implantable medical or therapeutic devices such as vascular endoprostheses, intraluminal endoprostheses, stents, coronary stents, peripheral stents, surgical and/or orthopedic implants for temporary use, such as surgical screws, plates, nails and other fastening means, permanent surgical or orthopedic implants, such as bone prostheses or joint prostheses. The skilled person in the art will understand that it can be as well applied to any of the following medical devices: biopsy needles, markers and such devices; breast tissue expanders; cardiovascular catheters and accessories; carotid artery vascular clamps; coils and filters; EGC electrodes; Foley catheter with temperature sensors; halo vests and cervical fixation devices; heart valve prostheses and annuloplasty rings; hemostatic clips; ocular implant and devices; otology implants; Patent ductus arteriosus (PDA), Atrial septal defect (ASD) and Ventricular septal defect (VSD) occluders; pellets and bullets; penile implants; vascular access parts, infusion pumps and catheters and so on.

The medical device according to the present invention comprises, or essentially consists of, a metallic substrate made of a material selected from the group consisting of iron, magnesium, nickel, tungsten, titanium, zirconium, niobium, tantalum, zinc or silicon and, if necessary, a second component of one or several metals from the group consisting of lithium, sodium, potassium, calcium, manganese, iron or tungsten, preferably of a zinc-calcium alloy. In a further practical example, the metallic substrate consists of a memory effect material of one or several materials from the group consisting of nickel titanium alloys and copper zinc aluminium alloys. In a further practical example, the metallic substrate of the medical device consists of stainless steel, preferably of a Cr—Ni—Fe steel, in this case, preferably the alloy 316L, or a Co—Cr alloy such as Phynox, Elgiloy and Cobalt-Chromium. In preferred embodiments of the present invention, the implantable medical devices are stents, in particular metal stents, preferably self-expanding stents, for example, disclosed in U.S. Pat. No. 7,588,597.

Usually, the surface composition (atomic ratio) of an alloy is different from its bulk composition because of segmentation of material caused during its manufacturing procedure. For example, although Phynox essentially consists of several metals such as 40 wt % Co, 20 wt % Cr, 16 wt % Ni, 7 wt % Mo and 2 wt % Mn, much higher concentration of chromium comparing to the concentration of cobalt is observed in the surface of a raw material of Phynox. Furthermore, since chromium oxide is a ferromagnetic material, the naturally or conventionally oxidized raw Phynox should exhibits artifact in MRI. Therefore, in order to provide the metallic substrate with an anti-artifact property, the atomic concentration of cobalt at the surface of a metallic substrate has to be increased to a certain level and a certain amount of cobalt atoms present in the surface has to be converted into the oxidized state which exhibits anti-ferromagnetic property.

A metallic substrate 1 comprised in a medical device according to present invention comprises cobalt and at least one or more metals which exhibit ferro- or ferri-magnetic (FFM) property in its oxidized state, such as chromium and iron. As shown in FIG. 1, the metallic substrate 1 has a metallic bulk layer 3 and an oxide layer 2 at the outermost surface of the metallic substrate 1. The oxide layer 2 comprises an anti-artifact layer 4 at the exterior surface of the oxide layer 2 which has at least 50%, preferably at least 60%, more preferably at least 70%, even more preferably at least 80%, still even more preferably at least 100% and most preferably at least 120%, of cobalt-atomic percent (at % Co) to the total amount of the metallic atoms which exhibit ferro- or ferri-magnetic property in its oxidized state, present within the anti-artifact layer 4. At least 90%, preferably 95%, more preferably all of cobalt atoms present in the anti-artifact layer 4 are oxidized into at least one of Co(II) and Co(III) oxidized state, such as cobalt monoxide (CoO), cobalt hydroxide ($Co(OH)_2$) and cobalt (II, III) oxide ($Co_3O_4$), and at least 55% of cobalt atoms present within the anti-artifact layer 4 are at least one of CoO and $Co_3O_4$. $Co_3O_4$ is also represented as $CoO.Co_2O_3$ and known as anti-ferromagnetic (AFM) property as same as CoO. Preferably, all cobalt atoms in the anti-artifact layer 4 are oxidized into CoO and/or $CoO.Co_2O_3$. The oxide layer 2 may further comprise a layer 5 containing a mixture of cobalt oxides and cobalt metal between the anti-artifact layer 4 and the metallic bulk layer 3. Said layer 5 may contain less than 50% of cobalt-atomic ratio (at % Co) to the total amount of metallic atoms which exhibit the FFM property in its oxidized state present within the anti-artifact layer 4.

In a preferred embodiment a metallic substrate 1 of an medical device comprises an oxide layer 2 at the outermost surface of the metallic substrate 1 containing at least 50% of cobalt-atomic percent (at % Co) to the total amount of metallic atoms which exhibit the FFM property in its oxidized state present within 10 nm from the external surface of the oxide layer 2, and at least 90%, preferably at least 95% of cobalt atoms, more preferably all cobalt atoms present within 10 nm from the external surface of the oxide layer 2 are converted into at least one of Co(II) oxidized state and Co(III) oxidized state such as cobalt monoxide (CoO), cobalt hydroxide ($Co(OH)_2$) and Co(II,III) oxide ($Co_3O_4$), preferably into CoO and/or $Co_3O_4$.

Cobalt oxides present at outermost surface of the oxide layer 2 according to the present invention acts as anti-artifact coating for a metallic substrate 1 with a certain cobalt-atomic concentration to the total amount of metallic atoms, and when used in MRI reduces the production of the artifacts caused by the magnetic property of the metallic substrate. As a result the tissues around a medical device comprising said metallic substrate becomes visible in the MRI process. For example, if the medical device has the form of a cylinder such as in a stent, cobalt oxides in the oxide layer 2 can provide visualization of the signal not only from the tissue therearound but also within the lumen thereof.

The anti-artifact layer 4 of the metallic substrate 1 according to the present invention has at least 50% of cobalt-atomic ratio (at % Co) to the total amount of metallic atoms which exhibit the FFM property in its oxidized state and at least 90%, preferably at least 95% of cobalt atoms, more preferably all cobalt atoms present in the anti-artifact layer 4 are oxidized into at least one of Co(II) oxidized state and Co(III) oxidized state.

A ratio of the thickness $T_{(4)}$ of the anti-artifact layer 4 to the thickness $T_{(1)}$ of the metallic substrate 1 should be at least 1/80000 (=$T_{(4)}/T_{(1)}$), preferably at least 1/8000, more preferably at least 1/4000, even more preferably at least 1/800.

The thickness of the anti-artifact layer 4 of the metallic substrate 1 is at least 1 nm, preferably at least 5 nm, more preferably at least 10 nm, even more preferably at least 100 nm, still even more preferably at least 500 nm, most preferably at least 1000 nm.

Surface compositions (atomic concentration at % of each metallic atom) of a metallic substrate have been measured with X-ray photoelectron spectroscopy (XPS). The surface cobalt-atomic concentration to the total amount of metallic atoms which exhibit the FFM property in its oxidized state present within 10 nm from the exterior surface of the metallic substrate according to the present invention is at least 50 at % Co, preferably at least 60 at % Co, more preferably at least 70 at % Co, even more preferably at least 80 at % Co, still even more preferably at least 100 at % Co, and most preferably at least 120 at % Co.

The present invention also provides a method for providing a metallic substrate 1 with an anti-artifact property in MRI. The method comprises the following steps:
(a) providing the metallic substrate 1;
(b) forming a cobalt-rich layer at the outermost surface of the metallic substrate 1, wherein the cobalt-rich layer comprises at least 30% of cobalt-atomic concentration (at % Co) to the total amount of metallic atoms which exhibit ferro- or ferri-magnetic property in its oxidized state present therein; and
(c) converting at least 90%, preferably at least 95%, more preferably all, of cobalt atoms present within at least 10 nm from the external surface of the metallic substrate (1) into at least one of cobalt (II) oxidized state and cobalt (III) oxidized state, such as cobalt monoxide (CoO), cobalt hydroxide (Co(OH)$_2$) and cobalt (II, III) oxide (Co$_3$O$_4$) and at least 55% of cobalt atoms present therein into at least one of CoO and Co$_3$O$_4$.

In order to improve the anti-artifact property, at least 55%, preferably at least 70%, of cobalt atoms present within at least 10 nm from the external surface of the metallic substrate 1 preferably all cobalt atoms present therein are converted into CoO or Co$_3$O$_4$ which has anti-ferromagnetic property.

If a cobalt-based alloy is selected as a metallic substrate for a medical device such as braided stent, the metallic substrate may be subjected to a thermal treatment so as to promote the cobalt-atomic percent (at % Co) to the total amount of metallic atoms which exhibit the FFM property in its oxidized state present within 10 nm from the exterior surface of the metallic substrate and increase the thickness of the oxidize layer at the outermost surface of the metallic substrate. The thermal treatment may be performed at a temperature at least 500° C., preferably at least 550° C., for at least 3 hours.

A cobalt-rich layer at outermost surface of a metallic substrate 1 can also be formed by physical vapor deposition (PVD) with a target comprising cobalt. In order to obtain directly an oxide layer 2 comprising high cobalt-atomic concentration, the metallic substrate may be subjected to physical vapor deposition (PVD) with a target comprising cobalt in presence of oxygen. By using physical vapor deposition (PVD) this method can be applicable to a metallic substrate containing neither cobalt nor nickel for obtaining an anti-artifact layer on the outermost surface of the metallic substrate. Physical vapor deposition (PVD) for the method according to the present invention may be selected from a group consisting of sputter deposition, evaporative deposition, pulsed laser deposition, electron beam physical vapor deposition, and cathodic arc deposition.

The metallic substrate 1 can also be subjected to an ethylene oxide atmosphere in a concentration between 500 mg/L and 1 g/L saturated with water at between 40° C. and 60° C. for at least 5 hours, preferably at least 10 hours so as to oxidized cobalt atoms present within the outermost layer of the metallic substrate into at least one of cobalt (II) and cobalt (III) oxidized states, such as cobalt monoxide (CoO) and cobalt (II,III) oxide (Co$_3$O$_4$).

The present invention also provides a use of a cobalt-rich composition as anti-artifact layer 4 covering a metallic substrate 1 placed into a MRI apparatus for reducing the production of artifacts in magnetic resonance imaging (MRI) caused by the magnetic property of the metallic substrate 1. The anti-artifact layer 4 is present at outermost surface of the metallic substrate 1 and has at least 30% of cobalt-atomic ratio (at % Co) to the total amount of metallic atoms which exhibit the FFM property in its oxidized state present within the anti-artifact layer 4, and at least 90%, preferably at least 95%, more preferably all, of cobalt atoms present within the anti-artifact layer 4 are converted into at least one of cobalt (II) oxidized state and cobalt (III) oxidized state, such as cobalt monoxide (CoO), cobalt hydroxide (Co(OH)$_2$) and cobalt (II, III) oxide (CoO.Co$_2$O$_3$), and at least 55 at % Co of oxidized cobalts therein are at least on of CoO and CoO.Co$_2$O$_3$.

EXAMPLES

Example 1

Four Phynox stents with internal expanded diameters of 6 mm and lengths of 2 cm according to the present invention were manufactured by braiding 48 to 56 wires of 60 to 80 μm of diameter as disclosed in U.S. Pat. No. 7,588,597. After braiding, the surface of two stents were subjected to a thermal treatment (TT) in an oven for 3 h at 550° C., and then, subjected to an ethylene oxide atmosphere saturated with water at 47° C. for 5 h (i.e., sample INV01) or for 10 h (i.e., sample INV02). The other two stents were further subjected to a chemical treatment (CT) (i.e., polishing with a mixture of nitric acid and hydrogen fluoride, following by passivation with nitric acid) after the thermal treatment, and then, subjected to an ethylene oxide atmosphere under same condition as described above for 5 h (i.e., sample INV03) or for 10 h (i.e., sample INV04).

Two Phynox stents with internal expanded diameters of 6 mm and lengths of 2 cm were manufactured as comparative samples by braiding as described above. After braiding, one stent was subjected neither to a thermal treatment (TT) nor to the ethylene oxide atmosphere (i.e., sample CEX01). Another stent was only subjected to the ethylene oxide atmosphere as described above for 5 h (i.e., sample CEX02).

Polyvinyl chloride tube filled with water (PVC+water) was prepared as a sample which has a same size as the samples. Since this tube does not have any artifacts caused by metal, a perfect image can be expected in MRI. Therefore, it is used as a reference of perfect image in MRI.

The cobalt-atomic percent to the total amount of chromium atoms which exhibit the FFM property in its oxidized state (i.e., Cr according to this example) present within 10 nm from the exterior surface of stent (at % (Co/Cr)), the atomic ratio of oxidized cobalt ($Co_{ox}$) to the total amount of cobalt atoms ($Co_{total}$) present within 10 nm from the exterior surface of stent (at % ($Co_{ox}/Co_{total}$)), and the cobalt-atomic percent in anti-ferromagnetic (AFM) forms ($Co_{AFM}$) (i.e., CoO and $CoO.Co_2O_3$) to the total amount of cobalt atoms present within 10 nm from the exterior surface of stent (at % ($Co_{AFM}/Co_{ox}$)) were measured with XPS and summarized in Table 1. The cobalt-atomic percent to total amount of chromium present in the exterior surface of CEX01 and CEX02 were only 16 and 29 at % (Co/Cr), while INV01, INV02, INV03 and INV04 exhibit 71, 263, 52, 90 at % (Co/Cr), respectively. The atomic ratio of oxidized cobalt present in the exterior surface of CEX01 and CEX02 are only 62 and 60 at % ($Co_{ox}/Co_{total}$) respectively, while INV01, INV02, INV03 and INV04 exhibit 92, 100, 90 and 100 at % $Co_{ox}/Co_{total}$, respectively.

MRI was performed at 1.5 T using Echospeed SR 120 (General Electrics Medical System) and the following pulse sequences:

Spin echo pulse sequence; repetition time (TR), 500 msec; echo time (TE), 20 msec; matrix size, 256×256; filed of view, 2 mm; section thickness, 0.2 mm; bandwidth, 32 kHz; and Gradient echo pulse sequence; repetition time (TR), 100-500 msec; echo time (TE), 15 msec; flip angle, 30 degrees; matrix size, 256×256; filed of view, 2 mm; section thickness, 0.2 mm; bandwidth, 32 kHz.

Figure 2:
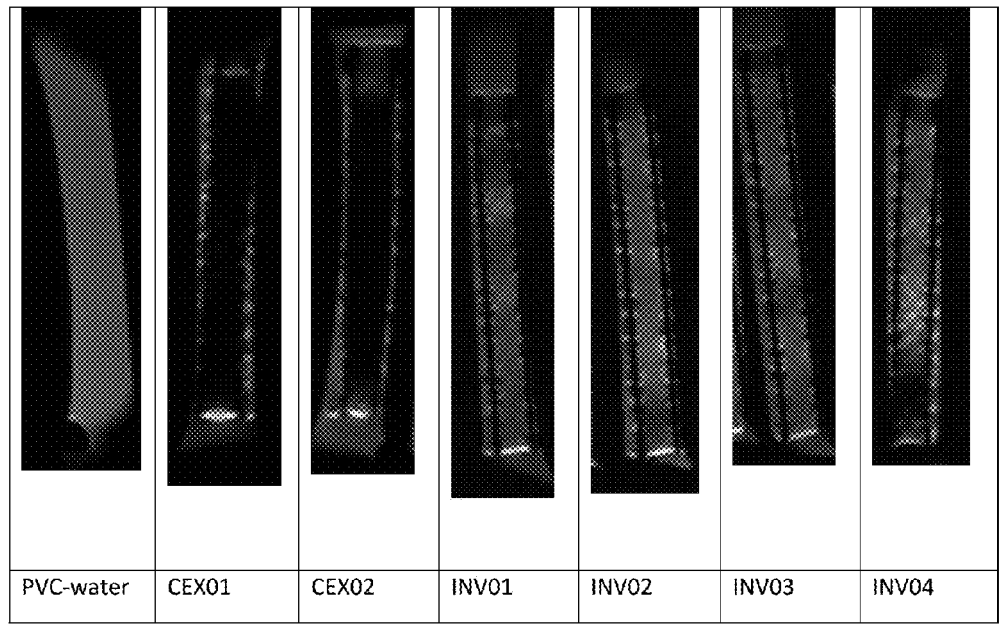
FIG. 2 shows Table 2a summarizing images of samples in longitudinal view obtained in MRI according to comparative tests.
Figure 3:
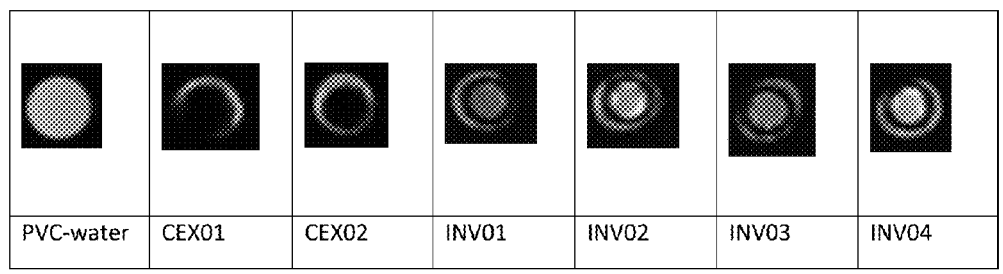
FIG. 3 shows Table 2b summarizing images of samples in cross direction obtained in MRI according to comparative tests.

Images of stents in MRI according to the present invention and comparative examples were analyzed for magnitude and spatial extent of signal loss within the lumen and outside the stent. The images in MRI are summarized in Tables 2a and 2b (FIGS. 2 and 3). The MRI compatibility of each stent was assessed by compared the MRI images and the results are summarized in Table 1 as MRI relative visibility.

Higher ratio of cobalt atomic ratio to chromium in the top 10 nm of the cobalt rich composition provides the anti-artifact layer with improved "mask" effect, resulted in that the MRI visibility was improved. Also higher cobalt atomic percent in oxidized state ($Co_{ox}$) to the total cobalt amount (at % ($Co_{ox}/Co_{total}$)) of the cobalt-rich composition enhanced the mask effect of the anti-artifact layer which leads to improvement of MRI visibility.

Example 2

A Phynox stent with internal expanded diameters of 35 mm according to the present invention was manufactured by braiding 90 to 112 wires of 190 μm of diameter so as to have three of interconnected layers as disclosed in U.S. Pat. No. 7,588,597. After braiding, the surface of stent was subjected to a thermal treatment (TT) in an oven for 3 h at 550° C., and then, subjected to an ethylene oxide atmosphere saturated with water at 47° C. for 5 h.

MRI was performed under same condition as indicated in Example 1, instead an ear plug made of polyethylene foam was disposed within the stent in order to evaluate the MRI visibility inside of the stent.

Figure 4:
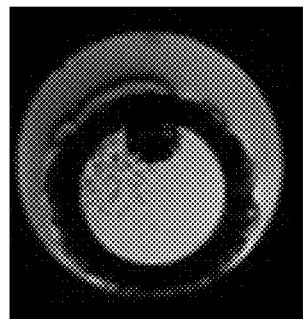
FIG. 4 shows a MRI image of a sample comprising an ear plug in cross direction obtained in MRI according to comparative tests.

Despite the fact that the stent was made of thicker and greater numbers of wires and having larger expanded diameter, the MRI visibility was assured inside and around the stent and the shape of ear plug was clearly detected in the image as shown in FIG. 4.

The invention claimed is:

1. A medical device comprising a metallic bulk layer as a metallic substrate comprising at least one of chromium and iron, and a cobalt-rich composition layered on an outermost surface of the metallic bulk layer, wherein within 10 nm from the external surface of the cobalt-rich composition:

TABLE 1

The atomic ratio of cobalt to chromium (at % (Co/Cr)), the cobalt-atomic percent in oxidized state to the total amount of cobalt atoms (at % ($C_{ox}/Co_{total}$)), the cobalt-atomic percent in AMF forms to the total amount of cobalt atom in oxidized state (at % ($C_{AFM}/Co_{ox}$)) in the top 10 nm of the stents, and MRI relative visibilities

|  | TT/TC | Oxidization time (h) (EtO/water) | at % (Co/Cr) | at % ($Co_{ox}/Co_{total}$) | at % ($Co_{AFM}/Co_{ox}$) | MRI visibility |
|---|---|---|---|---|---|---|
| CEX01 | Non | non | 16 | 62 | 55 | poor |
| CEX02 | Non | 5 h | 29 | 60 | 56 | poor |
| INV01 | TT | 5 h | 71 | 92 | 55 | Good |
| INV02 | TT | 10 h | 263 | 100 | 70 | Very good |
| INV03 | TT + CT | 5 h | 52 | 90 | 56 | Good |
| INV04 | TT + CT | 10 h | 90 | 100 | 71 | Very good |

As shown in FIGS. 2 and 3, respectively, sample according to comparative examples (CEX01 and CEX02) caused significant signal loss and did not allow for visibility of the lumen. Surprisingly, samples with a cobalt-rich composition comprising cobalt in oxidized state as anti-artifact layer according to the present invention (INV01 and INV03) caused only minor outbreak of artifacts, even allowed for visualization of the signal from within the lumen almost. The MRI images provided with INV01 and INV03 are almost clear as the one provided with the PVC tube filled with water. Improved MRI images were obtained with the samples which were subjected to an ethylene oxide atmosphere for 10 h (i.e., samples INV02 and INV04) with greater cobalt atomic percent being in AFM form to the total amount of cobalt atom in oxidized state (at % ($Co_{AFM}/Co_{ox}$)), i.e., 70 at % and 71 at % respectively.

the cobalt-atomic percent (at %) is at least 50 at % to the total amount of chromium and/or iron atoms present in the metallic substrate;

at least 90 at % of the cobalt atoms are oxidized into at least one of Co(II) and Co(III) oxidized state to the total amount of cobalt atoms; and at least 55 at % of the cobalt atoms are at least one of cobalt monoxide (CoO) and cobalt (II,III) oxide ($CoO.Co_2O_3$) to the total amount of cobalt atoms in oxidized state.

2. The medical device according to claim 1, wherein, within 10 nm from the external surface of the cobalt-rich composition, at least 95 at % of the cobalt atoms are oxidized into at least one of Co(II) and Co(III) oxidized state to the total amount of cobalt atoms.

3. The medical device according to claim 1, wherein within 10 nm from the external surface of the cobalt-rich composition, the cobalt-atomic percent is at least 60 at % to the total amount of chromium and/or iron atoms present in the metallic substrate.

4. The medical device according to claim 1, wherein:
the cobalt-rich composition further comprises at least 50 at % of cobalt atoms to the total amount of chromium and/or iron atoms present in the metallic substrate between 10 and 5000 nm from the external surface of cobalt-rich composition layer; and
at least 90% of the cobalt atoms are oxidized into at least one of Co(II) and Co(III) oxidized state to the total amount of cobalt atoms within at least 100 nm from the external surface of the cobalt-rich composition layer.

5. The medical device according to claim 1, wherein the medical device is implantable and selected from a group consisting of vascular endoprosthesis, intraluminal endoprosthesis, stent, coronary stent, peripheral stent, filter and heart valve.

6. The medical device according to claim 1, wherein the metal substrate comprises a biocompatible alloy selected from the group consisting of stainless steel and a Co—Cr alloy.

7. The medical device according to claim 1, wherein the outermost layer of the cobalt-rich composition layer comprises at least 50 at % of cobalt atom to the total amount of chromium and/or iron atoms present in the metallic substrate;
at least 90% of the cobalt atoms to the total amount of cobalt atoms are oxidized into at least one of Co(II) and Co(III) oxidized state in the outermost layer of the cobalt-rich composition layer;
at least 60% of the cobalt atoms to the total amount of cobalt atoms in oxidized state are at least one of cobalt monoxide (CoO) or cobalt (II,III) oxide (CoO.$Co_2O_3$) in the outermost layer of the cobalt-rich composition layer; and
a ratio of the thickness of the outermost layer of the cobalt-rich composition layer to the thickness of metallic substrate is at least 1/80000.

8. A method for providing a metallic substrate with an anti-artifact property in magnetic resonance (MR) imaging comprising
(a) providing a metallic bulk layer as a metallic substrate comprising at least one of chromium and iron;
(b) forming a cobalt-rich composition as a layer at an outermost surface of the metallic substrate, wherein the cobalt-rich composition layer comprises at least 50% of cobalt-atomic percent (at % Co) to the total amount of chromium and/or iron atoms present in the metallic substrate; and
(c) converting at least 90% of the cobalt atoms present within at least 10 nm from the external surface of the cobalt-rich composition layer into at least one of Co(II) oxidized state and Co(III) oxidized state, while converting at least 55% of the cobalt atoms present therein into at least one of cobalt monoxide (CoO) and cobalt (II,III) oxide (CoO.$Co_2O_3$),
thereby producing the medical device of claim 1.

9. The method according to claim 8, wherein the cobalt-rich composition comprises at least 60% of cobalt-atomic ratio (at % Co) to the total amount chromium and/or iron atoms present in the metallic substrate.

10. The method according to claim 8, wherein in step (a) the metallic substrate is in a form selected from a group consisting of wire, plate, cylinder and any shape of an implantable device.

11. The method according to claim 8, wherein the metallic substrate is a Co—Cr alloy and subjected to a thermal treatment at a temperature at least 500° C. for at least 3 hours in step (b).

12. The method according to claim 8, wherein in step (b) the metallic substrate is subjected to physical vapor deposition (PVD) with a target comprising cobalt so as to form a cobalt-rich composition as a layer on the metallic substrate.

13. The method according to claim 8, wherein, in step (b), the metallic substrate is subjected to physical vapor deposition (PVD) with a target comprising cobalt in the presence of oxygen so as to form a cobalt-rich composition as a layer on the metallic substrate, wherein the cobalt is in an oxidized state.

14. The method according to claim 12, wherein PVD is selected from a group consisting of sputter deposition, evaporative deposition, pulsed laser deposition, electron beam physical vapor deposition, and cathodic arc deposition.

15. The method according to claim 8, wherein the thickness of the cobalt-rich composition layer is at least 1 nm.

16. The method according to claim 8, wherein in step (c) the coated metallic substrate is subjected to an ethylene oxide atmosphere in a concentration between 500 mg/L and 1 g/L saturated with water at a temperature between 40° C. and 60° C. for at least 5 hours.

17. A method of providing a magnetic resonance (MR) image comprising performing imaging with a medical device comprising a metallic bulk layer as a metallic substrate comprising at least one of chromium and iron and a cobalt-rich composition as an anti-artifact layer that continuously covers a least one surface of the metallic substrate,
wherein within 10 nm from the external surface of the cobalt-rich composition:
the cobalt-atomic ratio to the total amount of chromium and iron atoms present in the metallic substrate is at least 50 at %;
at least 90 at % of the cobalt atoms are in at least one of Co(II) oxidized state and Co(III) oxidized state to the total amount of cobalt atoms;
at least 55 at % of the cobalt atoms are at least one of cobalt monoxide (CoO) and cobalt (HMI) oxide (CoO.$Co_2O_3$) to the total amount of cobalt atoms in oxidized state; and
a production of artifacts in the magnetic resonance imaging (MM) caused by a ferro- or ferri-magnetic property of the metallic substrate is reduced compared to an MR image provided by the same medical device without the cobalt-rich composition layer.

18. The method according to claim 13, wherein PVD is selected from a group consisting of sputter deposition, evaporative deposition, pulsed laser deposition, electron beam physical vapor deposition, and cathodic arc deposition.

* * * * *